(12) United States Patent
Hasegawa

(10) Patent No.: US 6,780,176 B2
(45) Date of Patent: Aug. 24, 2004

(54) EYESIGHT CORRECTING APPARATUS

(76) Inventor: Tokuichiro Hasegawa, 61-1, Aza-Ryuu, Shinmaiko, Chita-city, Aichi-ken (JP)

( * ) Notice: Subject to any disclaimer, the term of this patent is extended or adjusted under 35 U.S.C. 154(b) by 0 days.

(21) Appl. No.: 10/267,312

(22) Filed: Oct. 8, 2002

(65) Prior Publication Data

US 2003/0088241 A1 May 8, 2003

(30) Foreign Application Priority Data

Nov. 6, 2001 (JP) ........................................ 2001-340149

(51) Int. Cl.[7] .............................................. A61B 18/18
(52) U.S. Cl. ......................................... 606/27; 607/104
(58) Field of Search ........................ 606/41, 4–6, 167, 606/27–28, 48–50, 166; 607/101–105

(56) References Cited

U.S. PATENT DOCUMENTS

| | | | | |
|---|---|---|---|---|
| 3,831,604 A | * | 8/1974 | Neefe | 604/207 |
| 4,381,007 A | * | 4/1983 | Doss | 606/27 |
| 5,616,139 A | * | 4/1997 | Okamoto | 606/4 |
| 5,779,696 A | * | 7/1998 | Berry et al. | 606/16 |
| 5,989,209 A | * | 11/1999 | Barrett | 604/22 |
| 6,024,095 A | * | 2/2000 | Stanley, III | 128/898 |
| 2003/0158567 A1 | * | 8/2003 | Ben-Nun | 606/167 |

FOREIGN PATENT DOCUMENTS

| WO | WO 99/39238 | * | 8/1999 |
|---|---|---|---|
| WO | WO 99/52460 | * | 10/1999 |

* cited by examiner

*Primary Examiner*—Michael Peffley
(74) *Attorney, Agent, or Firm*—Michael J. Striker

(57) ABSTRACT

The present invention provides a apparatus for correcting eyesight characterized in that a cornea pressure member is slidably attached to a cap-like cornea sucking member, and a cooling liquid injection channel is formed through the cornea pressure member. The cornea sucking member is further provided with an air sucking port and a liquid ophthalmic medicine injection port. The cornea sucking member is applied to a cornea which has been softened by being warmed by any known warming method; said member pulls the cornea forward by sucking air through the air sucking port; and in the mean time the cornea pressure member presses the cornea with its head portion so as to modify the shape of the cornea to a desired one. Immediately thereafter, a cooling liquid is passed through the cooling liquid injection channel to rapidly cool the cornea, thereby stabilizing the corrected shape of the cornea.

5 Claims, 5 Drawing Sheets

EYESIGHT CORRECTING APPARATUS

BACKGROUND OF THE INVENTION

1. Field of the Invention

The present invention relates to an eyesight correcting apparatus for correcting myopia, hyperopia and astigmatism, particularly an eyesight correcting apparatus for recovering the eyesight by correcting the shape of the cornea.

2. Detailed Description of Prior Art

The eyeball has a structure consisting of, from front, the cornea followed by a crystalline lens, a vitreous body and the retina. Rays of light carrying an image passing through the cornea is converged by the crystalline lens, transmitted through the vitreous body and focused onto the retina. The image focused onto the retina is transmitted through the optic nerve connected to the retina to the brain center. The periphery of the crystalline lens is suspended with a ciliary body (ciliary zonule): the thickness of the lens is adjusted through the tension or relaxation of the ciliary body, so that the refraction of the lens may vary so as to focus the image on the retina.

Generally, the blurred vision in myopia or hyperopia can be accounted for by two mechanisms: one relates to a lowered refracting power of the crystalline lens (refractive myopia or hyperopia) which may result from the lowered functional state of the tissues such as the ciliary body responsible for adjusting the thickness of the crystalline lens as a result of exertion or aging; and the other relates to abnormal elongation of the visual axis (axial myopia or hyperopia), that is, the axis passing through the crystalline lens and retina (sclera and choroid), which may develop even when the refracting power of the lens remains normal. The axial myopia may be observed in an eyeball where the cornea and the lens are abnormally close to each other, or where the cornea is abnormally convex forward.

In any case, in myopia, when a far point is viewed, the rays from that point are brought to a focus in front of the retina, while in hyperopia, when a near point is viewed, the rays therefrom are brought to a focus behind the retina. Moreover, because the corneal surface does not represent a perfect sphere, it has more or less spherical aberrations and astigmatism, and this abnormality is compensated for generally by the crystalline lens. If this optical apparatus is disordered, astigmatism will result.

Conventionally, for the correction of myopia, hyperopia and astigmatism, spectacles and contact lenses have been employed. However, those apparatuses present with a number of disadvantages: they are cumbersome because they must be worn and removed before and after each use; and they can not be used by those who are engaged in vigorous sports or in occupations requiring only the use of unaided eyes. To compensate for those disadvantages, eyesight correcting methods have been developed and actually practiced.

The simplest method among them aims at activating the crystalline lens, and the ciliary body which is responsible for adjusting the lens: the method consists of ordering the patient to look into a cylindrical apparatus like a telescope, and to watch, in the cylinder, an object or a printed image while the object is physically moved back and forth, that is, to track the movement of the object by vision, and of resolving the impaired vision through the repetition of this exercise. However, with this method, the notable effect appears only after the patient has repeated the exercise for several tens minutes everyday for a certain period. Thus, the method requires a considerable time before it has a notable effect, that is, the method is slow in action.

Recently, the method based on laser radiation (called "LASIK") is employed for the correction of myopia. This method consists of ablating the central portion of the cornea with a diameter of about 3 to 15 mm around the center of the pupil using a laser beam, so that the front-end surface of the cornea is made flat or concave. Then, the cornea serves as a concave lens, and incident rays of light carrying an image come to be appropriately refracted by the cornea, and thus the image is properly focused on the retina.

However, this method requires a high skill from the surgical operator, is highly risky, and may cause an anxiety in the patient because of the smallness of the previously treated cases, as to what change the operated cornea will undergo over several years ahead. In addition, if unfortunately the operation were unsuccessful, the operated cornea could not recover the original condition. Moreover, because the depth of ablation has a certain limitation, the method cannot be applied for correcting the high degree of myopia. As it is, for correcting the high degree of myopia, there is a known method that depends on the implantation of an intraocular lens. However, this method is not always reliable because it is not yet thoroughly clarified what complications the operation may cause, and the method is not applicable to the patients with cataract or iritis.

Recently, an eyesight correction method called "ortho-keratology" has attracted attention. This eyesight correction method consists of attaching a contact lens having a prescribed form to the cornea before the patient goes to bed, thereby adapting the cornea to take a specified shape during sleep. However, this eyesight correction method also has its own drawbacks: although the patient can maintain normal eyesight for a certain period after the correction contact lens is removed, the cornea resumes thereafter its original shape owing to its elasticity, that is, its eyesight correction effect is temporary, and the patient must repeat the same cornea correction procedure using the prescribed contact lens everyday, to ensure the correction effect; and further because the prescribed contact lens has a use life of several years, the patient must replace it periodically which will require a considerable cost.

As discussed above, there is no conventional correction method that is applicable to all the types of ophthalmic abnormalities. Particularly, even with the aforementioned method based on laser radiation or on ortho-keratology, it is difficult to securely correct the eye suffering from serious myopia/hyperopia, and the eye in which the cornea is depressed towards the crystalline lens.

SUMMARY OF THE INVENTION

As a result of a long-lasting study, the present inventor found that warming the cornea which is composed of keratin compounds to a specified temperature or higher softens it, and succeeded in developing a novel eyesight correction method comprising softening the cornea by warming it by any known method, modifying the shape of the softened cornea as appropriate according to the abnormal eyesight, so as to compensate for the abnormality, and quenching the thus modified cornea so that the corrected cornea may not restore its original shape owing to its elasticity.

An object of this invention is to provide such an apparatus for correcting eyesight.

Another object of this invention is to provide an eyesight correcting apparatus capable of easily correcting the deformed cornea safely without inflicting any damage to it, and of enabling the operated cornea to maintain the corrected shape over a long period or semi-permanently.

A still further object of this invention is to provide an eyesight correcting apparatus capable of, even when applied to the eye suffering from the high degree of myopia or hyperopia, or to the cornea whose front surface is depressed towards the crystalline lens, safely and securely correcting the deformed cornea in such a manner as to enable the cornea to maintain the corrected shape after the operation.

A still further object of this invention is to provide an eyesight correcting apparatus, which is so simple in structure that it is producible at a low cost, and easy for handling.

The present invention relates to an apparatus for correcting eyesight by modifying the shape of the cornea, which comprises a cornea pressure member for shaping the cornea by pressure, a warming unit of the cornea pressure member, and a cooling unit for cooling the cornea.

The present invention further comprises a micro-vibration generating unit for applying a micro-vibration to the cornea pressure member.

The present invention further comprises a cornea sucking member for modifying the shape of the cornea by sucking, in addition to or instead of the cornea pressure member.

When the eyesight correcting apparatus of this invention is used, it is necessary to soften the cornea in advance by warming the eyeball by any known method.

The cornea pressure member is for modifying the shape of the softened cornea to any desired shape such as a convex or concave spherical shape, flat shape, etc., according to the given condition to be corrected. Its material may be chosen from any synthetic resins, metals, non-metal elements, etc., as long as it is safe and sanitary even when it is brought into contact with the cornea. The cornea pressure member may apply a pressure on the cornea in the form of a hydrostatic pressure or an air pressure.

The warming unit of the cornea pressure member is for maintaining the softened state of the cornea produced at a preparatory stage, and for preventing the temperature of the cornea from being lowered through the contact with the pressure-based cornea shaping unit. The warming unit may be based on nickel-chromium wire heating, module alloy heating, laser heating, microwave heating, warm water reflux heating, etc. If the cornea pressure member is based on hydrostatic or air pressure, it is possible to utilize pressurized water or air heated to a predetermined temperature.

The cornea cooling unit is for rapidly cooling (quenching) the operated cornea kept at a warm state, thereby stabilizing the corrected shape of the cornea. The unit may take any desired shape and structure as long as the above object is satisfied, and is permanently or detachably attached to the cornea pressure member, independently of the cornea sucking member. The cooling mode may include water- or air-cooling. One preferred example of the cornea cooling unit operates by ejecting a cooling liquid kept in a syringe or pipette towards the cornea from the injection port of the cornea sucking member.

The cornea warmed to a predetermined temperature or higher is softened: tissue cells become relaxed and expanded. Therefore, it is possible to correct the shape of the cornea with the aforementioned cornea shaping member and then to stabilize the corrected shape by rapidly cooling the cornea via a cooling liquid, because then the tissue cells of the cornea contract in a moment to stabilize the corrected shape. This quenching procedure resembles quite well the quenching of a metal, which comprises rapidly cooling a metal modified in texture by previous heating to stabilize the modified metal texture so firmly that the metal will never resume the original texture over time. Similarly, this procedure prevents the operated cornea from resuming the original shape.

The micro-vibration generating unit may be used a small vibrator adjustable in the rate and intensity of vibrations, and is for applying a micro-vibration to the cornea via the cornea pressure member. This unit facilitates the tissue cells of the cornea, which have been subjected to warming to be further, softened and activated. It is also possible to modify the shape of the cornea bit by bit through the pressure worked via the micro-vibration.

The cornea sucking member takes, for example, a semi-spherical, cap-like form, and when it is attached to the cornea, a defined space is formed between the inner surface of the cap and the front surface of the cornea. The radius (R) of the cap can be varied to any desired value to match the given corrected shape of the cornea.

The vacuum sucking unit may incorporate any sucking machine such as a small vacuum pump, suction syringe, vacuum vessel containing a cartridge with an evacuated internal space, etc., as long as it has a sucking power sufficiently strong to cause the softened cornea to bulge forward. The cornea sucking unit may be provided with the aforementioned warming unit.

According to the present invention, the cornea pressure member may be combined with the cornea sucking member such that it can be slid over the latter.

According to one embodiment of this invention, the cornea sucking member takes a cap-like shape, and it causes a negative pressure to develop in the space between the member and the front surface of the cornea, in such a manner as to cause the cornea to be modified in its shape. The cornea pressure member comprises a rod portion which penetrates the cornea sucking member to slide therethrough, and a head portion attached to the distal tip end of the rod portion. A cooling liquid injection channel is formed through both the rod and head portions.

The cornea sucking member has a medicine injection port through which it is possible to dispense a liquid medicine to the cornea as needed, so that the surface of the cornea can be kept moist, and thus the cornea be prevented from drying and hardening which would otherwise result during the cornea being subject to the correction procedure.

DESCRIPTION OF PREFERRED EMBODIMENTS

The preferred embodiments of this invention will be described with reference to the attached drawings, in conjunction with the underlying eyesight (visual acuity) correction methodology.

Figure 1:
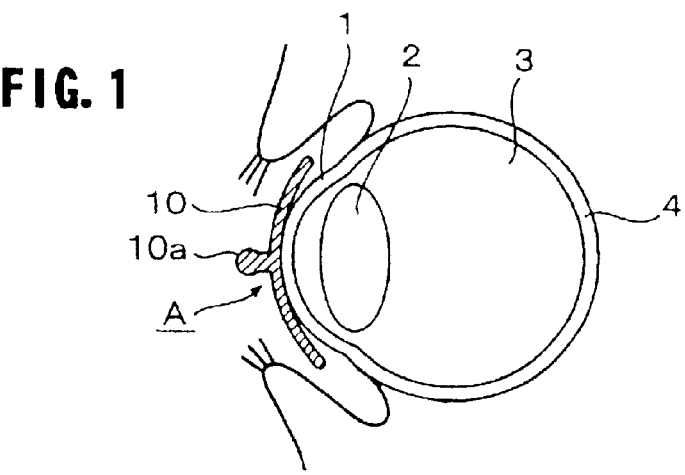
FIG. 1 is a sketchy view of an eyesight correcting apparatus A representing a first embodiment of this invention, which showing a cornea pressure member is applied to the cornea.
Figure 2:
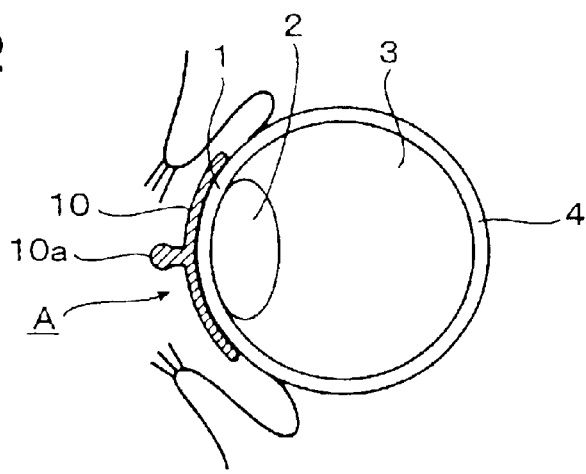
FIG. 2 is a sketchy view of the eyesight correcting apparatus A of this invention, which showing the cornea changes its shape when a pressure is applied thereto through the cornea pressure member.

As shown in FIGS. 1 and 2, roughly speaking an eyeball comprises a transparent cornea 1 and a crystalline lens 2 followed by a retina 4 with a vitreous body 3 inserted in between. The cornea 1 bulges slightly forward to take a spherical shape. The crystalline lens 2 is suspended by a ciliary body (not showing). The ciliary body expands or contracts the crystalline lens 2 via its tension or relaxation, thereby altering the refractive index of the lens in such a manner as to cause an image carried by light to be properly focused on the retina 4. In myopia, rays from a far point are brought to a focus in front of the retina 4, while in hyperopia, rays from a near point are brought to a focus behind the retina 4.

The ophthalmologist (operator) firstly examines the condition of the myopia, hyperopia or astigmatism: which causes the impaired vision, abnormal refraction of the lens or abnormal elongation of the visual axis; and whether the cornea 1 is normal, that is, whether the cornea 1 is not abnormally bulged forward nor abnormally depressed backward. After having decided that the patient has symptoms indicated for the treatment, the operator subjects him/her to the eyesight correction treatment based on the eyesight correction apparatus operating as described below.

For the eyesight correction therapy according to this invention, it is necessary to warm the cornea 1 to a predetermined temperature (for example 38 to 45° C.) so that the cornea 1 can be sufficiently softened. Warming the cornea 1 may occur by any known method based on, for example, a disposable body warmer, infra-red ray radiation heater, incandescent lamp, module alloy heater, polymer crystal warmer, towel soaked with warm water, etc.

The most preferred among them is the eye-mask previously proposed by the inventors (U.S. patent application, Ser. No. 10/120,344). This eye-mask is for relieving an eyestrain by warming the eye with a disposable body warmer or the like, and by then applying a magnetic force or micro-vibration to the eye, thereby softening the cornea, ciliary body and other tissues to relax them. This eye-mask also includes an eye-contact pad, which is effective for modifying the shape of the cornea. Therefore, being based on warming, and magnetic and vibratory effects given in combination, this eye-mask can even correct the impaired vision of myopia or hyperopia, if the impairment results from exertion or is mild in degree.

Figure 3:
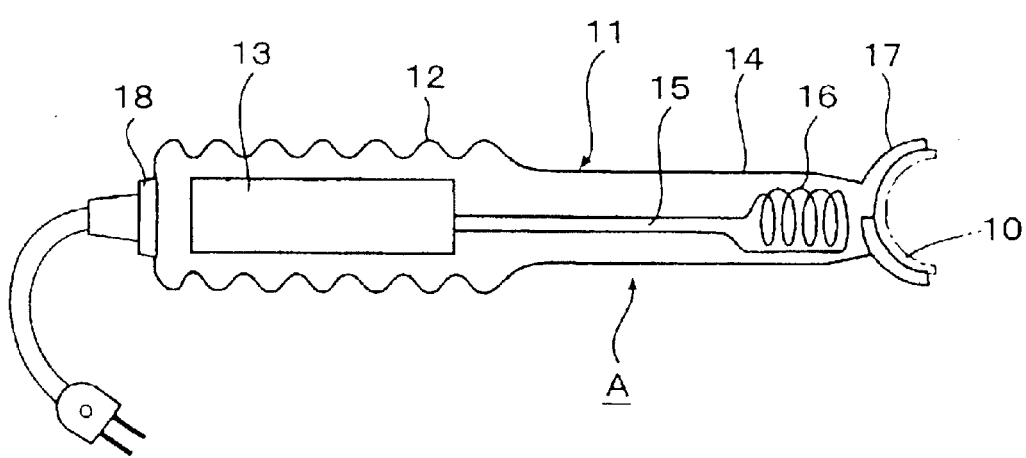
FIG. 3 is an overview of the eyesight correcting apparatus A representing the first embodiment of this invention.

The eyesight correcting apparatus A as shown in FIGS. 1 to 3 is the simplest of all the embodiments of this invention. Specifically, as shown in FIG. 1, this method comprises, after having sufficiently softened the cornea 1 by the above method, applying a cornea pressure member 10 to the cornea 1 as is done for a contact lens, and applying a pressure to the cornea 1 bulging forward until the cornea takes a shape as indicated in FIG. 2 so that rays from a far point or from a near point are properly focused on the retina 4. Prior to this operator, it is necessary to warm the cornea pressure member 10 to an appropriate temperature to prevent the temperature of the cornea 1 from falling.

In this particular embodiment, the cornea pressure member 10 takes an externally bulged spherical shape, and has a knob 10a on its external surface. The usable material for the cornea pressure member 10 may include synthetic resins, glass, metals, non-metal elements, etc. that are not harmful to the living body. In this particular embodiment, a copper material which has an excellent heat conductivity is used. The copper material has its surface finely processed and finished, and is plated with gold and nickel-chromium. The cornea pressure member 10 is prepared in various forms to match the various shapes of the cornea to be corrected: some have spherical shapes with different diameters; and others have a surface inwardly bulged, a flattened surface and a rod-like shape.

FIG. 3 shows the main body 11 of the apparatus for warming the cornea pressure member 10 to a predetermined temperature and for applying a micro-vibration to the cornea. The main body 11 has a slender cylindrical case 14, which has on its front end a spherical connector socket 17 for detachably receiving the cornea pressure member 10. The casing includes a grip portion 12 which contains in its interior a unit 13 for generating a micro-vibration by a certain known method, and the micro-vibration generating unit 13 has an extended rod 15 to the distal tip end of which is attached a warming unit 16 based on a nickel-chromium heater or the like. The casing 14 has on its back end a controller 18 that regulates the intensity of the vibration generated by the micro-vibration generating unit 13, and the temperature of the warming unit 16.

The cornea pressure member 10 is attached to the connector socket 17 of the main body 11, and the warming temperature and micro-vibration generated by the warming unit 16 and micro-vibration generating units 13 are transmitted via the cornea pressure member 10 to the cornea 1. If the cornea 1 is softened in a sufficiently brief time as a result of this treatment, it will be possible to dispense with the pre-warming of the cornea which will be required as a preliminary when the eye-mask is used for the correction.

When the cornea pressure member 10 is pressed lightly or hard depending on given situations against the cornea 1 while the cornea is being warmed and subjected to micro-vibration, the cornea is modified in its shape in accordance with the shape of the internal surface of the cornea pressure member 10. The time required for this reshaping of the cornea will be short when the patient is young and his/her corneal cells are sufficiently elastic. However, the time in question will be long when the patient is elderly because then the corneal cells become stiff as a result of aging.

However, generally, in several to several tens minutes the cornea becomes sufficiently softened, except for certain rare cases.

Later, the cornea pressure member 10 is removed from the cornea 1, and the unaided eyesight of the operated eye is determined. When the unaided eyesight of the operated eye is found to be short of the normal eyesight or of the desired eyesight, the cornea correction operation is repeated. During this process, if the cornea 1 can readily resume its previous softened state in the presence of heat provided anew by the warming unit 16 incorporated in the main body 11 of the apparatus, warming by the eye-mask can be dispensed with.

If the eye is tested for its visual acuity, and found to be properly corrected, the cornea pressure member 10 is applied anew to the cornea as needed, and the cornea 1 is warmed with the warming unit 16 to a predetermined temperature. Immediately thereafter, the cornea pressure member 10 is removed from the cornea 1, and a cooling liquid (kept, for example, at 4 to 9° C.) stored in a syringe or pipette is ejected towards the center of the cornea 1. The ejection volume may vary according to the condition of the cornea, but is usually at a level of about 2 to 10 cc.

As a result of this cooling treatment, the tissue cells at the center of the cornea 1 contract to harden; the corrected shape of the cornea is thereby stabilized; and the cornea correcting treatment is completed. If the patient is unsatisfied with the treatment result, the treatment may be practiced anew by repeating the same procedures until the desired result is obtained. Thus, this treatment can modify the shape of the cornea to any desired one. It is not necessary to introduce a treatment specifically directed towards astigmatism, because astigmatism is naturally corrected when the associated myopia is corrected with the cornea pressure member 10.

The above-described eyesight correction apparatus A is effective for correcting the impaired vision of an eyeball in which the cornea 1 is normal, or in which the cornea 1 abnormally bulges forward. However, this apparatus will be ineffective for treating hereditary myopia and axial myopia in which the visual axis including the sclera and choroid is abnormally long. If an attempt were made to treat the impaired vision based on such an abnormally long visual axis by resorting only to the cornea correction therapy, the cornea 1 would have to be modified too much; the cornea itself could not endure such an extensive operation; and the cornea 1, even if it were corrected, might come into contact with another ocular element such as the crystalline lens 2. In order to treat such a case without causing the above complications, it is recommended prior to the introduction of the cornea correction treatment to resort to a priming treatment spending a considerable time for the procedure. The priming treatment comprises reducing the internal pressures of aqueous humor and of vitreous humor contained respectively in the space between the cornea 1 and the crystalline lens 2 and in the vitreous body 3, or warming the eyeball using, for example, the eye-mask proposed by the inventors, and applying a pressure and micro-vibration to the cornea using an eye-contact pad incorporating a magnetic body, to make the cornea susceptible to the succeeding cornea correction treatment.

Figure 4:
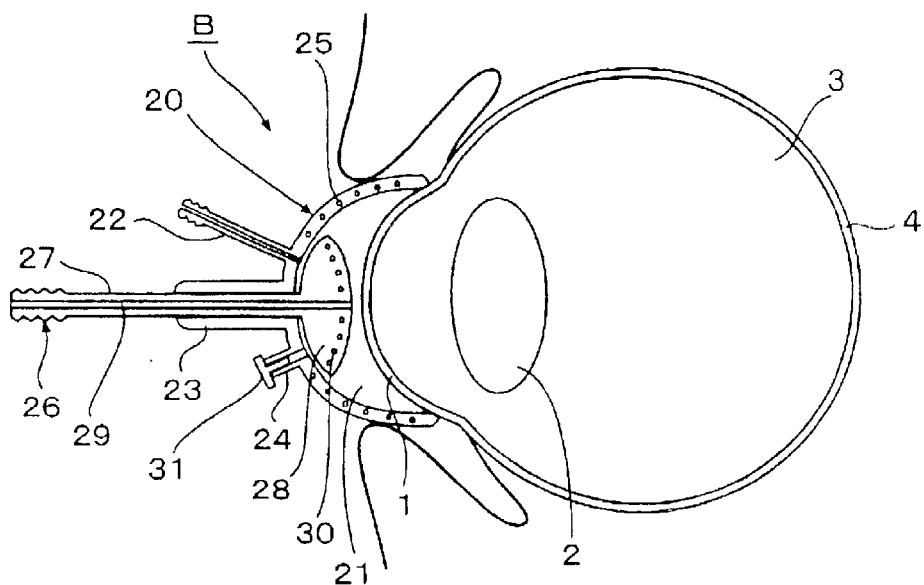
FIG. 4 is a sketchy view of another eyesight correcting apparatus B representing a second embodiment of this invention, which showing the apparatus is applied to the cornea.
Figure 5:
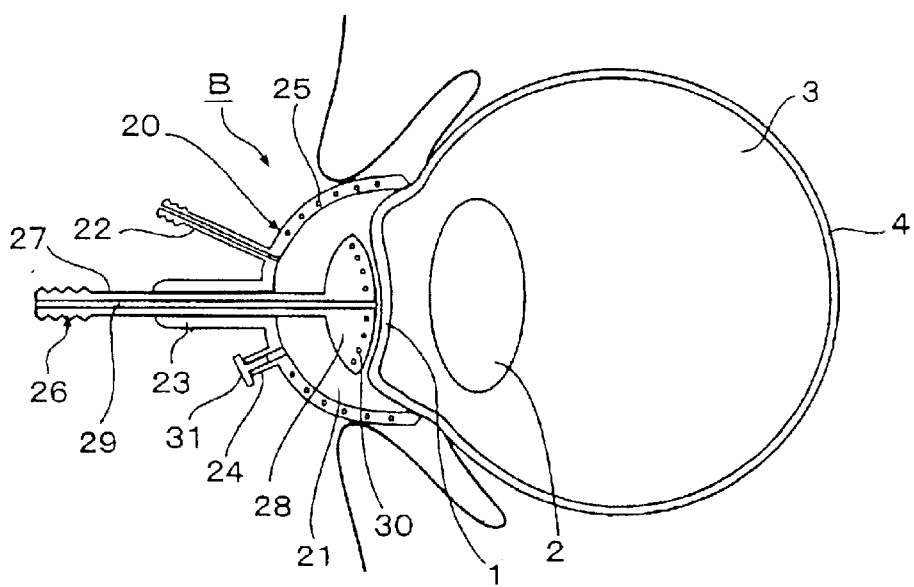
FIG. 5 is a sketchy view of the eyesight correcting apparatus B of this invention, which showing the apparatus modifies the shape of the cornea for correction by applying a pressure thereto.

FIGS. 4 to 7 relate to further embodiments of the eyesight correcting apparatus for precisely correcting the shape of the cornea which are extensions of the eyesight correcting apparatus A: FIGS. 4 and 5 to a apparatus for myopia and astigmatism, while FIGS. 6 and 7 to a apparatus for hyperopia and astigmatism.

Firstly, the eyesight correcting apparatus B shown in FIGS. 4 and 5 will be described. This apparatus is most effective for treating an abnormal eyeball for which the pressure-based shaping of the cornea 1 as shown in FIGS. 1 and 2 is likely to be ineffective, that is, an eyeball where the cornea 1 is abnormally shifted towards the crystalline lens 2 regardless of whether it suffers from refractive or axial myopia/hyperopia.

This eyesight correcting apparatus B comprises a cornea sucking member 20 taking a spherical cap-like shape, and a cornea pressure member 26 inserted into the cornea sucking member 20. The material for the cornea sucking member 20 and the cornea pressure member 26 may be any desired one as long as it is not harmful to the living body, and may include, as indicated above, synthetic resins, glass, metals, non-metal elements, etc.

The cornea sucking member 20 is so configured that, when it is applied to the cornea 1, a space 21 is formed between it and the surface of the cornea. The space 21 is evacuated to produce a negative pressure there, which sucks the cornea 1 towards it. The object of this procedure is to pull the cornea 1 apart from the crystalline lens 2, and to stabilize the cornea sucking member 20 with respect to the cornea 1 by sucking, so that a cornea pressure member 26 can apply a pressure precisely to a target spot on the cornea 1.

The cornea sucking member 20 comprises an air sucking port 22, another port 23 through which the cornea pressure member 26 is inserted, and a liquid ophthalmic medicine injection port 24. The cornea sucking member 20 is further provided with a heating member 25 based on a nickel-chromium heater, module alloy heater, laser heater, microwave heater, warm water reflux heater, etc. The heater can heat the cornea sucking member 20 to any desired temperature under the control of a temperature controlling unit not showing here. Several types of the cornea sucking members 20 different in shape and radius are prepared to match the various shapes of the cornea to be corrected.

The cornea pressure member 26 is slidably inserted through the cornea pressure member insertion port 23 towards the cornea 1. The cornea pressure member 26 comprises a rod portion 27 and a head portion 28, and a cooling liquid injection channel 29 runs through the central axis of those portions. In this particular embodiment, the head portion 28 takes a convex, spherical shape. However, it may take a concave, spherical shape, flat shape, etc., depending on the shape of the cornea to be corrected. Another heating member 30 based on a nickel-chromium heater, module alloy heater, etc., like the above one is incorporated in the head portion 28. The heater can heat the head portion 28 to any desired temperature under the control of a temperature controlling unit not illustrated here.

A vacuum-sucking machine (not showing) such as a vacuum pump or the like is connected to the air suction port 22 of the cornea sucking member 20, while a cylinder and a cooling water supply unit (not showing) such as a water feed pump are connected to the back end of the cornea pressure member 26. In this particular embodiment, the cooling liquid consists of physiological saline whose salt concentration is the same with that of tear. The liquid ophthalmic medicine injection port 24 is kept closed with a hermetically sealing plug 31 such as a cap while it is not used.

Next, how the shape of the cornea is corrected with the eyesight correcting apparatus B will be described. It should be understood, however, that the numerical values cited in the following explanation are given only for illustration, and never with an intention to limit the operation of the invention to them. Firstly, the aforementioned eye-mask kept at 40 to 42° C. is applied to the eyelid for 10 to 15 minutes, so that the underlying cornea can be sufficiently softened. In the mean time, the heating members 25 and 30 incorporated in the cornea sucking member 20 and the cornea pressure member 26 of the eyesight correcting apparatus B respectively are activated so that they are heated to 40 to 42° C. A cooling liquid filling the cylinder is kept at 4 to 9° C.

After confirming that the cornea 1 has been sufficiently softened, the operator removes the eye-mask, and immediately moves the cornea sucking member 20 which has been sterilized by heating towards the cornea 1 while holding the cornea pressure member insertion port 23 to bring the member 20 in contact with the cornea 1. Prior to this operation, it is necessary to apply an ophthalmic gelatinized antiseptic agent to the part of the cornea sucking member 20 which will come into direct contact with the cornea 1, as well as to the surface of the cornea 1.

After having applied the cornea sucking member 20 onto the cornea 1, the vacuum-sucking machine is switched on, to suck air in the space 21 through the air suction port 22. Thus, as shown in FIG. 5, the cornea sucking member 20 sucks such that the cornea bulges forward and that the cornea sucking member 20 is stabilized against the cornea 1. Through this operation, the cornea 1, even when it is abnormally shifted towards the crystalline lens 2, is forced apart from the latter.

The apparatus B is maintained at this state for 6 to 8 minutes, and the heating member 25 incorporated in the cornea sucking member 20 may be reheated as needed to maintain the softened state of the cornea 1. If the surface of the cornea 1 is dried in the mean time, the softness of the cornea 1 will be impaired. To avoid this, it is necessary to remove the hermetically sealing plug 31 applied to the liquid ophthalmic medicine injection port 24, to inject 0.5 to 1.0 cc of a common ophthalmic aseptic agent to the surface of the cornea 1 using a pipette, and to immediately close hermetically the port by reapplying the plug 31 thereto. In this operation, it is necessary to use a liquid ophthalmic agent heated at 40 to 42° C. Injection of the ophthalmic agent must be repeated at 4 to 5 minute intervals, so that the cornea 1 is kept moist.

After having completed the injection of a liquid ophthalmic medicine, the cornea pressure member 26 is advanced, until its head portion 28 is pressed against the cornea 1, and the shape of the cornea is modified in accordance with the shape of the head portion 28. In this process it is recommended to advance the cornea pressure member 26 step by step until the member is displaced by 2 to 5 mm. For this purpose, it is recommended to print a scale along the rod portion 29 of the cornea pressure member 26, because then the pressing advancement of the head portion 28 will be precisely controlled.

After confirming that the cornea 1 is modified by the cornea pressure member 26 so much as to take a prescribed shape, the operator switches off the heating members 25, 30, and immediately injects 5 to 10 cc of the cooling liquid through the cooling liquid injection channel 29 of the cornea pressure member 26 towards the central part of the cornea 1 from the head portion 28. This cools the tissue cells of the cornea 1, which has been softened, so rapidly that the modified shape of the cornea is stabilized in the manner as described above.

Then, the vacuum-sucking unit is switched off; the hermetically sealing plug 31 of the liquid ophthalmic medicine injection port 24 is opened; and air outside is allowed to enter into the space 21 enclosed by the cornea sucking member 20, so that the cornea sucking member 20 is separated from the cornea 1. The operator removes the cornea sucking member 20 while holding the cornea pressure member insertion port 23.

As a result of the above procedures, the cornea 1 is modified to take a concave shape in accordance with the shape of the head portion 28 of the cornea pressure member 26. This completes the first session of the vision correction therapy. The patient is then tested for his/her visual acuity. If it is found that the patient does not show the desired eyesight, the second session of the vision correction therapy will be started several days later. For the second session, another head portion 28 for the cornea pressure member 26 which has a spherical cap of a smaller radius should be employed, and only minute modification of the cornea 1 should be provided.

If the tissue cells constituting the cornea 1 is harder than normal as a result of aging or the like, the priming treatment, or heating the eyelid with the eye-mask should occur at 41 to 45° C., that is, at a temperature slightly higher than that required for the eye with a normal elasticity. Similarly, the heating members 25 and 30 of the cornea sucking member 20 and of the cornea pressure member 26 should be heated to 41 to 45° C. Then, the pressure applied by the cornea pressure member 26 against the cornea 1 should be kept lower than the corresponding one applied to the normal cornea. The correction operation for the cornea 1 with the pressure-based shaping member 26 should occur at smaller stepwise displacements over a longer time than is required for the normal eye.

With the aforementioned eyesight correcting apparatus B, the cooling liquid and the liquid ophthalmic medicine are injected from the respective ports. However, it is possible to inject either of the cooling liquid and the liquid ophthalmic medicine from the head portion 28 to selectively pass through the cooling liquid injection channel 29 alternately, or alternatively to employ the liquid ophthalmic medicine as a cooling liquid. In the latter case, an additional temperature control unit is introduced for controlling the temperature of the liquid ophthalmic medicine such that the liquid ophthalmic medicine can have a certain specified temperature when injected during the shaping of the cornea, and another specified temperature when injected during the quenching of the cornea. The eyesight correcting apparatus B may be further provided with a main body 11 like the one described above with respect to the eyesight correcting apparatus A such that it can additionally give a micro-vibration to the cornea.

Next, a eyesight correcting apparatus C shown in FIGS. 6 and 7 that is for treating hyperopia/astigmatism will be described. The eyesight correcting apparatus C comprises a cap-like cornea sucking member 20: the member 20 has an air suction port 22 and a liquid ophthalmic medicine injection port 24 at its center, and incorporates a heating member 25 in its spherical portion. A vacuum-sucking unit such as a vacuum pump is connected to the air sucking port 22, and the liquid ophthalmic medicine injection port 24 is hermetically closed by a hermetically sealing plug 31. The heating member 25 is the same with the one contained in the aforementioned eyesight correcting apparatus B. Several types of cornea sucking members 20 with various spherical portions having different radii are prepared.

How hyperopia is treated with this eyesight correcting apparatus C will be described. Generally, hyperopia is associated with the too short visual axis including the sclera and choroid, and thus when the cornea is bulged forward, normal vision will be obtained. For this purpose, the operator examines in advance the deformation of the hyperopic cornea and its degree. After confirming that the cornea is normal in its texture, the operator chooses a cornea sucking member 20 with a spherical portion having a radius appropriate for the cornea to be treated.

Firstly, in the same manner as described above with respect to the treatment of myopia, the operator warms the eyelid with an eye-mask by putting the mask kept at 37 to 45° C. on the eyelid for 5 to 15 minutes, so as to sufficiently soften the cornea 1. In the mean time, the heating member 25 of the cornea sucking member 20 is preheated to 40 to 42° C.

The moment the operator finds the cornea 1 has been sufficiently softened, he/she brings the cornea sucking member 20 into contact with the cornea 1, and warms it by heating the heating member 25 to 40 to 45° C. for 4 to 15 minutes. Meanwhile, air is sucked from the air sucking port 22 of the cornea sucking member 20 to produce a specified negative pressure in a space 21, to thereby pull forward the cornea 1 for 4 to 15 minutes. Meanwhile, in the same manner as above, a warmed liquid ophthalmic medicine is injected from the liquid ophthalmic medicine injection port 24 onto the cornea 1.

Figure 7:
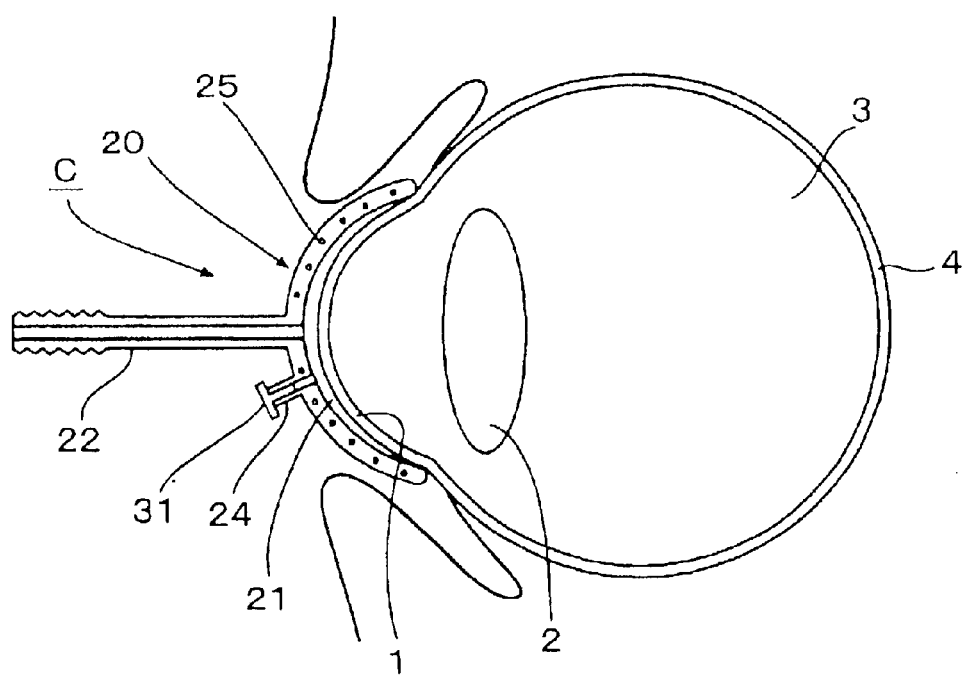
FIG. 7 is a sketchy view of the eyesight correcting apparatus C of this invention, which showing the apparatus modifies the shape of the cornea for correction by applying a pressure thereto.

As a result of this procedure, the cornea 1 bulges forward to make its front surface correspondent with the spherical surface of the cornea sucking member 20 as shown in FIG. 7, that is, to take a prescribed shape. The air suction port 22 may be pulled forward as needed so as to lightly pull the cornea sucking member 20 in the same direction, so as to force the cornea 1, if it is abnormally close to the crystalline lens 2, away from the crystalline lens 2.

After confirming that the cornea 1 has been properly corrected, the operator switches off the heating member 25, and opens the hermetically sealing plug 31 applied to the liquid ophthalmic medicine injection port 24, thereby returning the internal pressure of the cornea sucking member 20 to normal, and releasing the cornea sucking member 20 from the cornea 1. Then, the cornea 1 is left to return to normal temperature. In contrast with the above therapy for myopia, this eyesight correction therapy does not depend on the reshaping of tissue cells of the cornea 1, but on the elongation of the cornea itself. Therefore, it must be avoided to contract relevant tissue cells by cooling the corrected cornea 1 via the cooling liquid. If the cornea 1 were quenched, the bulged cornea 1 would return to the original size or worse would take a size below the original one.

Further, because the cornea itself is elongated by this operation, it is necessary, for example, in the treatment of an eyeball whose cornea has been degenerated as a result of aging, to repeat the above therapeutic procedures several times, or to employ cornea sucking members 20 having different spherical shapes from the initial one as needed, thereby gradually modifying the shape of the cornea to a prescribed one.

Figure 6:
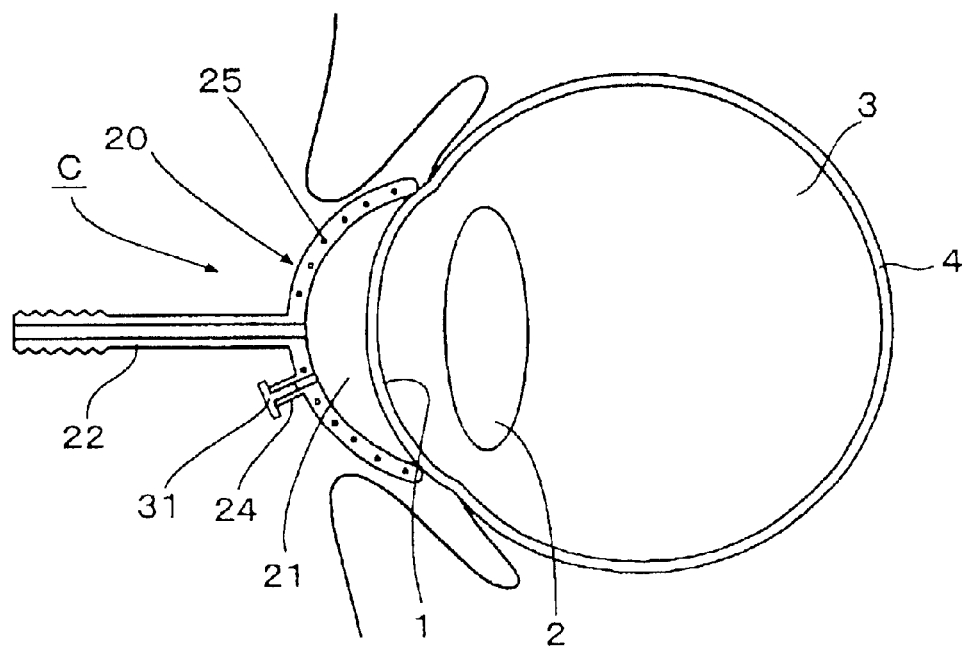
FIG. 6 is a sketchy view of a still other eyesight correcting apparatus C representing a third embodiment of this invention, which showing the apparatus is applied to the cornea.
Figure 8:
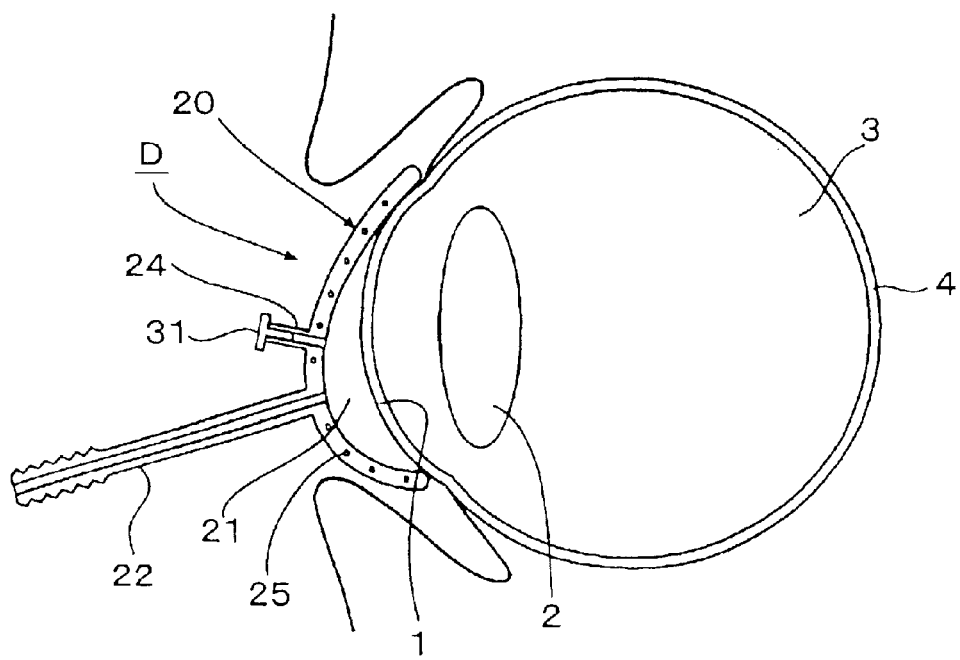
FIG. 8 is a sketchy view of a still other eyesight correcting apparatus D representing a fourth embodiment of this invention, which showing the apparatus is applied to the cornea.
Figure 9:
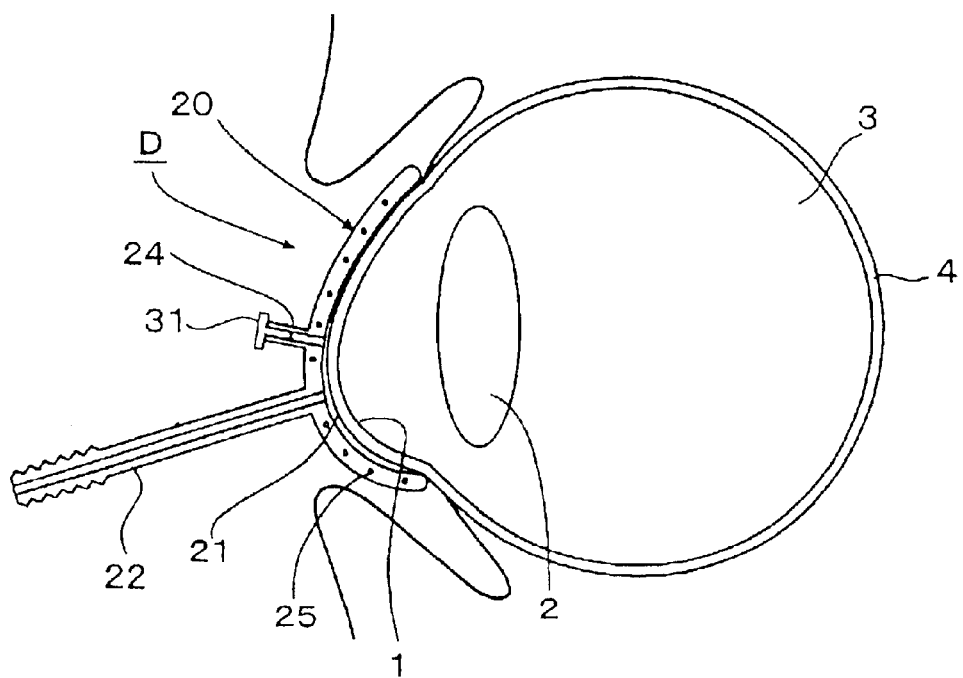
FIG. 9 is a sketchy view of the eyesight correcting apparatus D of this invention, which showing the apparatus modifies the shape of the cornea for correction by applying a pressure thereto.

A still further eyesight correcting apparatus D shown in FIGS. 8 and 9 is a variant of the aforementioned eyesight correcting apparatus C shown in FIGS. 6 and 7, which is suitable for correcting an eye so that the eye can cope with both myopia and hyperopia.

With this eyesight correcting apparatus D, the cornea sucking member 20 takes a cap-like, eccentric spherical shape with its lower portion more markedly bulged. It has an air sucking port 22 and a liquid ophthalmic medicine injection port 24 on the more markedly bulged lower portion. The other constitutive elements are the same with those of the eyesight correcting apparatus C shown in FIGS. 6 and 7.

According to the eyesight correcting apparatus D, when air is sucked from a space surrounded by the cornea sucking member 20 via the air sucking port 22, the cornea 1 is modified in its shape to take an eccentric spherical shape with its lower portion more markedly bulged in accordance with the shape of the cornea sucking member 20 as shown in FIG. 9. The cornea is kept at this state for a specified time. Or, the above procedure is repeated several times as needed to modify the shape of the cornea 1 step by step so that proper correction can be achieved. Then, the cornea 1 is left to be cooled to normal temperature in the manner as described above. This treatment can modify the shape of the cornea 1 to such a degree as to allow the eye to cope with both myopia and hyperopia.

Figure 10:
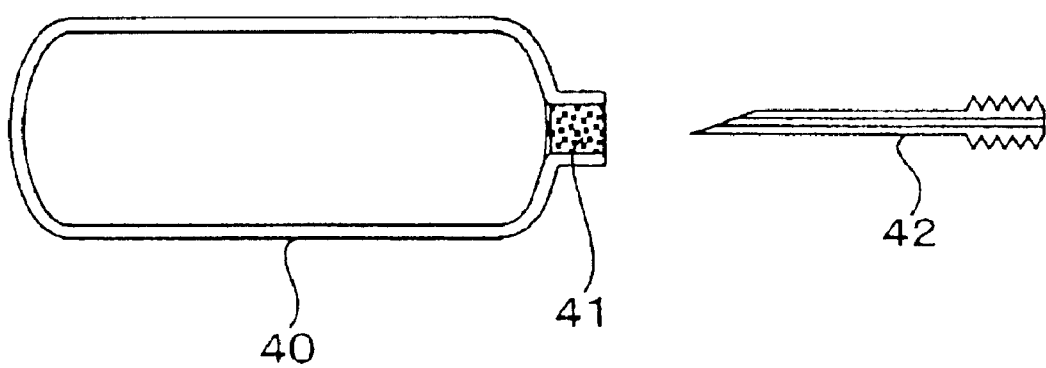
FIG. 10 is a sketchy view of an embodiment of the vacuum sucking unit of this invention.

FIG. 10 shows a cartridge type vacuum-sucking unit for sucking the cornea 1. The vacuum-sucking unit comprises a vacuum vessel 40 whose internal space is evacuated (for example, its vacuum pressure is 0.5 to 4 Kg), and a connecting needle 42 to be inserted through a hermetically sealing plug 41 of the vacuum vessel 40. During use, the end of the connecting needle 42 is connected via a tube to the air sucking port 22, while the tip end of the same needle 42 is inserted through the hermetically sealing plug 41 into the interior of the vacuum vessel 40. Then, being influenced by the vacuum pressure of the vacuum vessel 40, air enclosed in the space 21 surrounded by the cornea sucking member 20 is reduced in its pressure, and thus it sucks the cornea 1 towards it.

If a number of types of vacuum vessels 40 different in capacity and vacuum pressure are prepared for this cartridge type air sucking unit, it will be convenient. In one variant, the connecting needle 40 is omitted, and instead the end of the air suction port 22 is allowed to have a needle-like tip (the tip is covered with a cap for safety while not in use). During use, the needle tip of the end of the air suction port 22 is inserted directly through the hermetically sealing plug 41 of the vacuum vessel 40.

The above described eyesight correcting apparatuses and eyesight correcting therapies based on the use of those apparatuses are cited only to illustrate the present invention, and they can be modified in various manners without departing from the spirit of the present invention. For example, the air suction port 22 and the cornea pressure member insertion port 23 of the cornea correction apparatus B shown in FIGS. 4 and 5 may exist as a concentrically arranged duplicate tube structure. Or, plural cornea pressure member insertion ports 23 arranged to have different directions are prepared so that the cornea 1 can be pressed by the plural cornea pressure members 26 from different directions.

What is claimed is:

1. An eyesight correcting apparatus for correcting eyesight by modifying a shape of a cornea and quenching a modified cornea for stabilizing a corrected shape of the cornea, comprising:

a cornea sucking member for pulling the cornea apart from a crystalline lens and applying a pressure target spot on the cornea, wherein the cornea sucking member takes a cap-like shape, wherein the sucking is brought by a negative pressure generated in a space between said cornea sucking member and a corneal surface through operation of a vacuum-sucking unit;

a cornea pressure member for modifying the shape of the cornea by pressure, comprising a rod portion, which slidably penetrates through the cornea sucking member, and a head portion attached to an end of the rod portion; and a cooling unit for quenching the cornea, wherein a cooling injection channel is formed through the rod and head portions.

2. An eyesight correcting apparatus according to claim 1, wherein the cornea sucking member is further provided with a liquid medicine injection port.

3. An eyesight correction apparatus according to claim 2, wherein the cornea sucking member is further provided with a warming unit for warming the cornea sucking member, and an air suction port connected to the vacuum-sucking unit.

4. An eyesight correction apparatus according to claim 3, wherein the vacuum-sucking unit is a cartridge type vacuum vessel whose internal space has a reduced pressure.

5. An eyesight correction apparatus according to claim 1, further comprising a micro-vibration generating unit for applying a micro-vibration to the cornea pressure member.

* * * * *